(12) United States Patent
Grum-Schwensen

(10) Patent No.: US 9,629,743 B2
(45) Date of Patent: Apr. 25, 2017

(54) OSTOMY APPLIANCE AND AN ADHESIVE WAFER FOR SUCH APPLIANCE

(75) Inventor: Christen Grum-Schwensen, Hillerød (DK)

(73) Assignee: Hollister Incorporated, Libertyville, IL (US)

( * ) Notice: Subject to any disclaimer, the term of this patent is extended or adjusted under 35 U.S.C. 154(b) by 850 days.

(21) Appl. No.: 13/256,471

(22) PCT Filed: Mar. 16, 2010

(86) PCT No.: PCT/EP2010/053330
§ 371 (c)(1),
(2), (4) Date: Oct. 12, 2011

(87) PCT Pub. No.: WO2010/106039
PCT Pub. Date: Sep. 23, 2010

(65) Prior Publication Data
US 2012/0029450 A1    Feb. 2, 2012

(30) Foreign Application Priority Data

Mar. 17, 2009  (EP) .................................... 09155337

(51) Int. Cl.
| | | |
|---|---|---|
| *A61F 5/448* | (2006.01) | |
| *A61F 5/443* | (2006.01) | |
| *A61F 5/445* | (2006.01) | |
| *A61L 24/00* | (2006.01) | |

(52) U.S. Cl.
CPC .............. *A61F 5/443* (2013.01); *A61F 5/445* (2013.01); *A61F 5/448* (2013.01); *A61L 24/00* (2013.01)

(58) Field of Classification Search
CPC ................................ A61F 5/443; A61F 5/448

USPC .......................................................... 604/344
See application file for complete search history.

(56) References Cited

U.S. PATENT DOCUMENTS

| | | | | |
|---|---|---|---|---|
| 3,439,677 A | * | 4/1969 | Bonfils ................... | A61F 5/441 604/333 |
| 3,604,421 A | * | 9/1971 | Pizzella .................. | A61F 5/443 604/335 |
| 3,825,005 A | | 7/1974 | Fenton | |
| 4,252,120 A | * | 2/1981 | Carpenter ............... | A61F 5/443 604/336 |

(Continued)

FOREIGN PATENT DOCUMENTS

| | | |
|---|---|---|
| EP | 1378218 B1 | 1/2004 |
| EP | 1 832 256 A2 | 9/2007 |

(Continued)

OTHER PUBLICATIONS

International Search Report, mailed Jan. 7, 2010 (3 pages).
Written Opinion, mailed Jan. 7, 2010 (4 pages).

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

The present invention concerns adhesive wafer for an ostomy appliance, said adhesive wafer being adapted for directly or indirectly securing an ostomy pouch to a person's skin, wherein the wafer comprises a starter hole surrounded by a plurality of cutting guidelines for enabling the person to cut the hole into a desired aperture size, wherein the cutting guidelines substantially converge with the starter hole at an upper region of the hole.

6 Claims, 3 Drawing Sheets

(56) References Cited

U.S. PATENT DOCUMENTS

Figure 1:
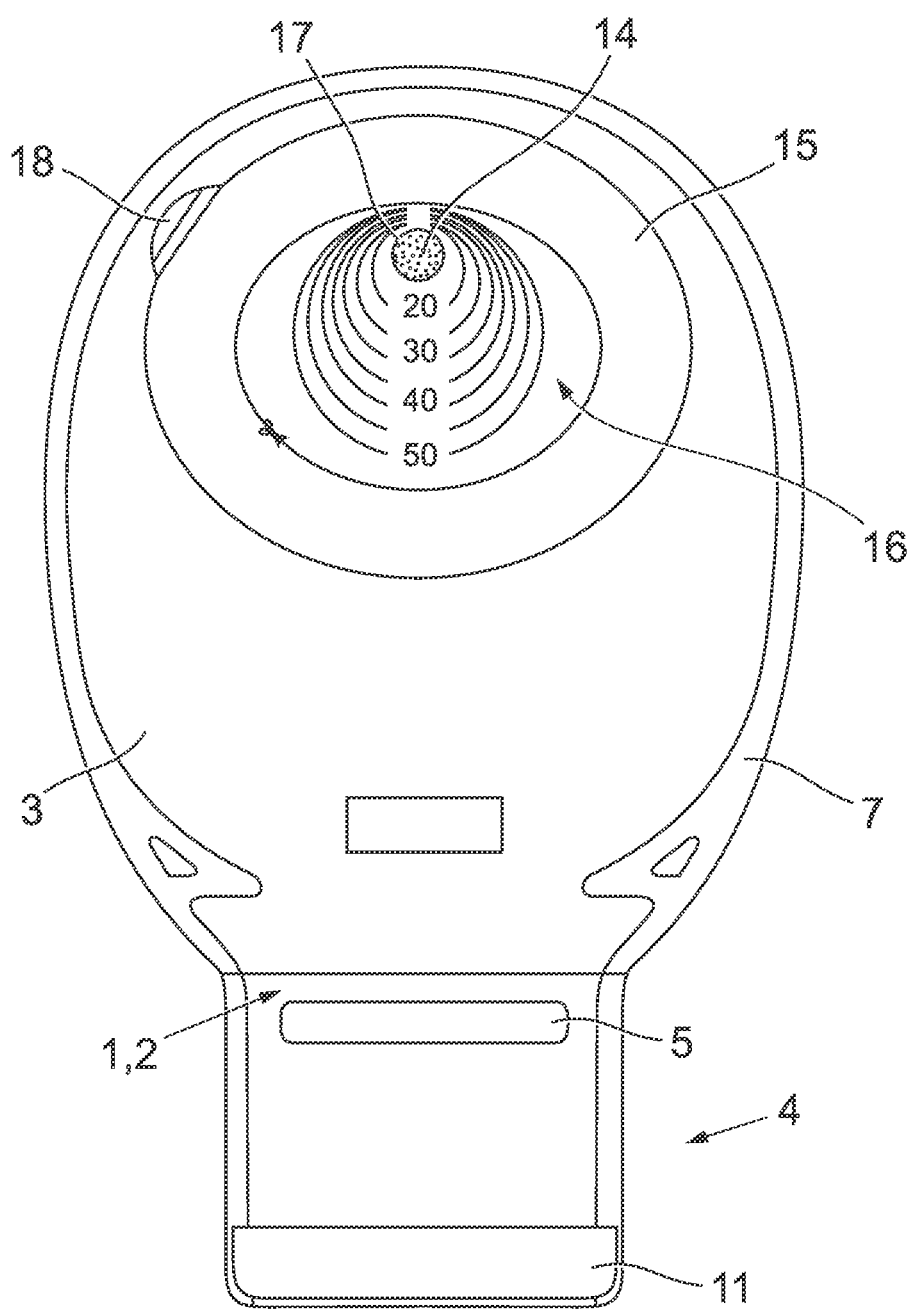

| | | | | |
|---|---|---|---|---|
| 4,372,308 | A * | 2/1983 | Steer | A61F 5/441 604/333 |
| 4,449,970 | A * | 5/1984 | Bevan | A61F 5/441 55/385.4 |
| 4,668,258 | A * | 5/1987 | Steer | A61F 5/441 55/385.4 |
| 4,681,574 | A * | 7/1987 | Eastman | A61F 5/443 604/344 |
| 4,938,750 | A * | 7/1990 | Leise, Jr. | A61F 5/441 55/385.4 |
| 5,486,158 | A * | 1/1996 | Samuelsen | A61F 13/025 602/43 |
| 5,690,622 | A * | 11/1997 | Smith | A61F 5/441 128/DIG. 24 |
| 5,690,623 | A * | 11/1997 | Lenz | A61F 5/441 604/332 |
| 5,938,647 | A * | 8/1999 | Smith | A61F 5/445 128/DIG. 24 |
| 5,976,118 | A * | 11/1999 | Steer | A61F 5/441 604/332 |
| 6,129,716 | A * | 10/2000 | Steer | A61F 5/441 604/332 |
| 6,165,159 | A * | 12/2000 | Blanton | A61F 5/441 604/333 |
| 6,332,879 | B1 * | 12/2001 | Nielsen | A61F 5/443 604/332 |
| D460,550 | S * | 7/2002 | Falconer | D24/118 |
| 6,659,989 | B1 * | 12/2003 | Otto | A61F 5/445 604/339 |
| 6,709,421 | B1 * | 3/2004 | Falconer | A61F 5/441 604/335 |
| 7,160,275 | B2 * | 1/2007 | Falconer | A61F 5/441 604/333 |
| 7,604,622 | B2 * | 10/2009 | Pedersen | A61F 5/448 604/333 |
| 7,722,585 | B2 | 5/2010 | Falconer et al. | |
| 2003/0060786 | A1 * | 3/2003 | Olsen | A61F 5/448 604/342 |
| 2005/0015065 | A1 * | 1/2005 | Falconer | A61F 5/441 604/335 |
| 2012/0029450 | A1 * | 2/2012 | Grum-Schwensen | A61F 5/443 604/344 |

FOREIGN PATENT DOCUMENTS

| | | |
|---|---|---|
| JP | 4571382 B2 | 10/2010 |
| WO | WO-93/00056 A1 | 1/1993 |
| WO | 9619164 A1 | 6/1996 |
| WO | WO-98/53771 | 12/1998 |
| WO | 9966859 A2 | 12/1999 |
| WO | WO-01/54632 A1 | 8/2001 |
| WO | 03065944 A1 | 8/2003 |
| WO | 2008134334 A1 | 11/2008 |

* cited by examiner

OSTOMY APPLIANCE AND AN ADHESIVE WAFER FOR SUCH APPLIANCE

REFERENCE TO RELATED APPLICATIONS

This is the U.S. national phase of International Application No. PCT/EP2010/053330, filed Mar. 16, 21010, which claims the priority benefit of European Patent Application No. EP 09155337.0, filed Mar. 17, 2009, the entire disclosures of which are incorporated herein by reference.

The present invention relates to an ostomy appliance comprising an adhesive wafer for directly or indirectly securing an ostomy pouch to a person's skin, wherein the wafer comprises a starter hole surrounded by a plurality of cutting guidelines for enabling the person to cut the hole into a desired aperture size.

The adhesive wafer of an ostomy appliance is normally provided with a small starter hole and concentric cutting guidelines printed on the wafer or printed on a release liner on the body side of the wafer around the starter hole so that the user can prepare the aperture in the wafer to fit the actual size of the stoma by cutting the inlet opening into the desired aperture size. Examples of such concentric cutting guidelines are disclosed in EP 0 984 750 B1 or EP 1 832 256 A2.

By the invention it is realized that it advantageous to provide an ostomy appliance comprising an adhesive wafer for directly or indirectly securing an ostomy pouch to a person's skin, wherein the wafer comprises a starter hole surrounded by a plurality of cutting guidelines for enabling the person to cut the hole into a desired aperture size, wherein the cutting guidelines substantially converge with the starter hole at an upper region of the hole.

Hereby the head space of the pouch is decreased which in turn means that a larger degree of filling of the pouch is achievable since the inlet opening is moved towards the top of the pouch. This is advantageous from a user's perspective as this satisfies the user wish for discrete pouches which can be hidden under the clothing. A low head space and a relatively smaller pouch which can be located lower on the user's body are achievable by the pouch according to the invention. Furthermore, a low fit also means that opening the pouch may be easier and consequently the pouch will be easier to empty in relation to drainable pouches since the outlet opening will be closer to the toilet.

Another advantage of achieving this lower head space is that this also results in a less prolapse of the pouch, i.e. the pouch will not hang as much outwards from the body when weight is applied.

By the term "converge" should be understood that the annular cutting guidelines come close together to each other or to the hole at one region but do not necessarily unite in a common point.

In preferred embodiment, the cutting guidelines substantially converge with the starter hole at a radial corresponding to the longitudinal direction of the pouch. Hereby, the "dead" volume in the head space in the top of the pouch may be minimized.

In an embodiment of the invention, the adhesive wafer is provided with a release liner on the body side and that the cutting guidelines are printed on said release liner. This facilitates the manufacturing of the adhesive wafer.

By the invention, it is realized that the off-centered starter hole with converging cutting guidelines may be used for different types of ostomy appliances. Accordingly, in one embodiment the pouch may be coupled to the proximal side of adhesive wafer by a mechanical or adhesive coupling, i.e. a two-piece solution. In another embodiment, the pouch may be permanently secured to the proximal side of adhesive wafer, i.e. a one piece solution.

Furthermore, the pouch may be a disposable or reusable pouch and either a closed pouch, a drainable pouch or a flushable pouch.

In relation to a two piece ostomy appliance, wafers may be supplied separately. Accordingly, in a second aspect of the invention, there is provided an adhesive wafer for an ostomy appliance, said adhesive wafer being adapted for directly or indirectly securing an ostomy pouch to a person's skin, wherein the wafer comprises a starter hole surrounded by a plurality of cutting guidelines for enabling the person to cut the hole into a desired aperture size, wherein the at least two cutting guidelines substantially converge with the starter hole at an upper region of the hole.

Figure 2:
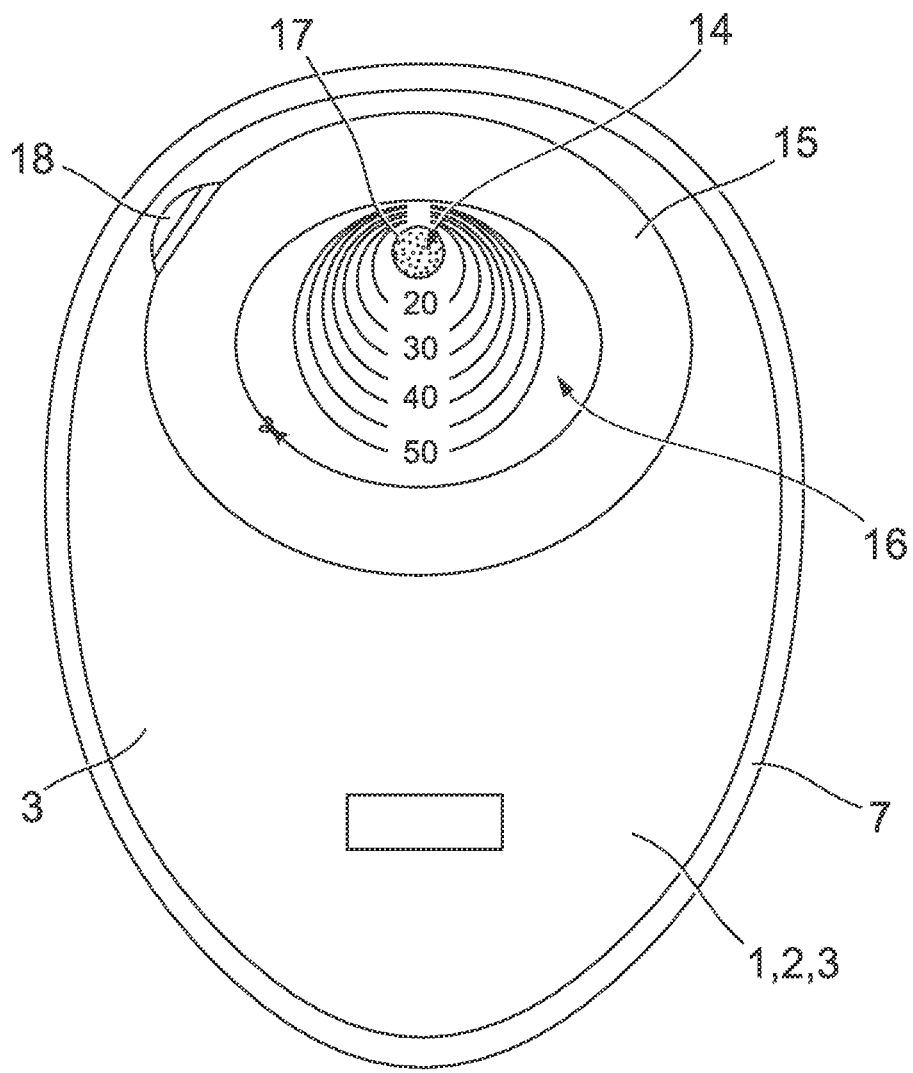
Figure 3:
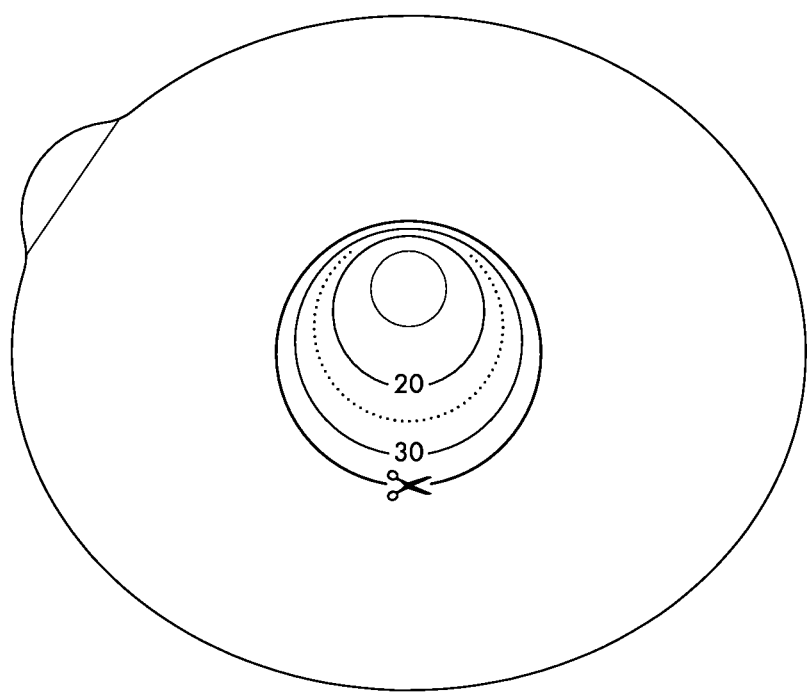

In the following the invention is described in further detail with reference to the accompanying drawings, in which FIG. 1 is a first embodiment of the invention where the adhesive wafer is in association with a drainable pouch shown from the body or proximal side;

FIG. 2 is a second embodiment of the invention where the adhesive wafer is in association with a disposable pouch shown from the body or proximal side; and FIG. 3 is an adhesive wafer according to a third embodiment of the invention shown from the body or proximal side.

With reference to FIGS. 1 and 2, the drainable ostomy pouch is an assembly of two sidewalls 1 and 2 where the proximal sidewall 1 is provided with an inlet 14 and the distal sidewall 2 which according to the embodiment shown is provided with a dressing panel or comfort layer 3. The side walls 1, 2 may be made of any suitable material, such as a flexible plastic material.

In FIG. 1 an embodiment of a pouch according to a first embodiment of the invention is shown. In the figure the pouch is shown from the body side. The product is provided with an inlet 14. Around the inlet there is provided an adhesive wafer or barrier material 15 for adhesively attaching the pouch to the skin of a user or to a face plate pre-mounted around the stoma of the user, when a release liner 18 is removed. The adhesive wafer 15 is provided with a small starter hole 17 and annular cutting guidelines 16 around the starter hole 17 printed on the wafer or printed on a release liner provided on the body side of the wafer, so that the user can prepare the adhesive wafer to fit the actual size of the stoma by cutting the inlet opening 14 into the right size.

The pouch according to the embodiment of FIG. 1 is provided with an outlet portion 4, which is provided with transversely extending bias members 11 on each of the two sidewalls 1, 2. The bias members 11 are preferably in the form of relative stiff but flexible, spring-like strips. The drainage portion 4 may be rolled around these bias member strips 11 and secured to a fastening strip 5 for closure of the pouch.

By the embodiments according to the invention shown in FIGS. 1-3, there is provided an off-centre starter hole 17 as it is realized that when the starter hole 17 is located off-centre rather than in the middle of the barrier 15 it is possible to locate the pouch lower on the body of the user and at the same time achieve a larger "active" volume as the head space in the pouch is decreased.

This is advantageous from a user's perspective as the user wants discrete pouches which can be hidden under the clothing. A low head space and a relatively smaller pouch which can be located lower on the user's body are achievable by the invention. Furthermore, a low fit also means that opening the pouch according to the first embodiment of FIG.

1 will be easier and consequently the pouch will be easier to empty since the outlet opening 4 will be closer to the toilet.

Another advantage of achieving this lower head space is that this also results in a less prolapse of the pouch, i.e. the pouch will not hang as much outwards from the body when weight is applied.

FIG. 2 shows a second embodiment of a pouch with an adhesive wafer according to the invention. In this embodiment, the pouch is a disposable pouch.

Although FIGS. 1 and 2 show pouches with an adhesive wafer for attachment directly onto the skin, i.e. a so-called one piece product, it is realized that the above described off-center starter hole solution may be used in relation to both one piece as well as two piece ostomy appliances. For use in a two piece embodiment FIG. 3 shows an embodiment of an adhesive wafer.

EXAMPLE

The pouch according to this embodiment of FIGS. 1 and 2 thus provides an increased active pouch volume when the starter hole of the pouch is off-centered towards the top of the pouch. A test has been made to verify if this is correct.

A regular size pouch with a 55 mm coupling ring was made with an Ø10 mm starter hole sitting 19 mm higher than if it was located in the center of the barrier. The pouch was attached to a plate in vertical position and water was filled in to the lower edge of a fictive Ø10 mm hole in the center. The volume was measured using a precision scale. Then more water was filled in order to reach the lower edge of the Ø10 mm off-centered hole and the volume was measured again. The difference between the two measurements was 56 g equal to 56 ml. The total volume of the pouch with off-centered starter hole was 569 ml. The increment was 10%.

In conclusion, the increment will depend on size and shape of the pouch and barrier, but it should be evident that an increase is obtainable on all constructions with off-centered starter hole sitting higher than the centre of the barrier.

As shown in FIGS. 1 and 2, the cutting guidelines 16 essentially converge with the starter hole 17 at the top of the hole 17, so that the cutting guidelines 16 substantially converge with the starter hole 17 at a radial corresponding to the longitudinal direction of the pouch. This enhances the effect of the off-centered starter hole.

With reference to FIG. 2 it is realized that the aspect of providing the pouch with an off-centered starter hole 17 may not only be provided on drainable pouches but may just as well be applied to closed or flushable pouches.

The invention is described above with reference to some preferred embodiments. However, it is realised that other variants may be provided without departing from the scope of the invention as defined in the accompanying claims.

The invention claimed is:

1. An ostomy appliance comprising an adhesive wafer for one of directly or indirectly securing an ostomy pouch to a person's skin, wherein the wafer comprises a starter hole surrounded by a plurality of cutting guidelines for enabling the person to cut the hole into a desired aperture size, and wherein the cutting guidelines are closer together to each other and to the starter hole at the outside of the starter hole adjacent its upper-most location in the adhesive wafer than a lower location.

2. An ostomy appliance according to claim 1, wherein the adhesive wafer is provided with a release liner on a body side and the cutting guidelines are printed on said release liner.

3. An ostomy appliance according to claim 1, wherein the pouch is coupled to a proximal side of the adhesive wafer by a mechanical or adhesive coupling.

4. An ostomy appliance according to claim 1, wherein the pouch is permanently secured to a proximal side of the adhesive wafer.

5. An ostomy appliance according to claim 1, wherein the pouch is one of a drainable, closed or flushable pouch.

6. An adhesive wafer for an ostomy appliance, said adhesive wafer being adapted for one of directly or indirectly securing an ostomy pouch to a person's skin, wherein the wafer comprises a starter hole surrounded by a plurality of cutting guidelines for enabling the person to cut the hole into a desired aperture size, and wherein the cutting guidelines are closer together to each other and to the starter hole at the outside of the starter hole adjacent its upper-most location in the adhesive wafer than a lower location.

\* \* \* \* \*